United States Patent [19]

Emblem et al.

[11] 3,975,202
[45] Aug. 17, 1976

[54] RIGID COHERENT GEL

[75] Inventors: Harold Garton Emblem, Bromley; John Andrew McPherson, Mirfield, both of England

[73] Assignee: Zirconal Processes Limited, Bromley, England

[22] Filed: Oct. 2, 1973

[21] Appl. No.: 402,751

[30] Foreign Application Priority Data
Oct. 4, 1972 United Kingdom............... 45809/72

[52] U.S. Cl................................. 106/65; 106/85
[51] Int. Cl.² ................... C04B 35/02; C04B 35/10
[58] Field of Search ............... 252/62, 317; 106/65, 106/85

[56] References Cited
UNITED STATES PATENTS

| | | | |
|---|---|---|---|
| 2,818,345 | 12/1957 | Vickers et al......................... | 106/65 |
| 3,615,778 | 10/1971 | Albert.................................. | 106/65 |
| 3,634,112 | 1/1972 | Yavorsky et al..................... | 106/65 |

*Primary Examiner*—J. Poer
*Attorney, Agent, or Firm*—Christensen, O'Connor, Garrison & Havelka

[57] ABSTRACT

A rigid gel is prepared by treating a solution of an aluminium hydroxyhalide solution of a specified formula and composition with an acetate or lactate accelerator. The invention has particular application to the preparation of refractories.

12 Claims, No Drawings

RIGID COHERENT GEL

SUMMARY OF THE INVENTION

This invention relates to the preparation of a rigid coherent gel from certain selected aluminium hydroxyhalides. The aluminium hydroxyhalides can be represented by the general formula $Al_2(OH)_nX_{(6-n)} \cdot m H_2O$ or a polymer thereof where $n$ is a number less than 6, $m$ is a number less than 4 and X represents a chlorine, bromine or iodine atom. Generally, the aluminium hydroxyhalides are solids, soluble in water or a mixture of water with alcohols, glycols, polyglycols or glycerol. In the above formula it is preferred that X is chlorine and $n$ has a value of 4 or greater.

According to the invention a rigid coherent gel is prepared by treating a solution of at least one aluminium hydroxyhalide of the above general formula in which $n$ has a value of 4 or greater, in water or a mixture of water and at least one alcohol, glycol, polyglycol or glycerol with an acetate or lactate which gives an aqueous solution that is alkaline. Desirably, the solution of the aluminium hydroxyhalide includes a substantial proportion of an aluminium hydroxychloride of the above general formula in which $n$ has a value of 4 or greater.

DETAILED DESCRIPTION OF THE INVENTION AND PREFERRED EMBODIMENTS

According to another aspect of the invention, shaped refractory articles are prepared by dispersing a refractory powder into a solution of at least one aluminium hydroxyhalide of the above general formula in which $n$ has a value of 4 or greater, in water or a mixture of water and at least one alcohol, glycol, polyglycol or glycerol, together with an acetate or lactate which gives an aqueous solution that is alkaline and while the dispersion is gelling, moulding the dispersion to shape during gelation and allowing the gelled dispersion to dry, then firing to obtain a refractory article.

The gelling time and the rigidity and coherent nature of the gel depend on the concentration of aluminium in the solution which is being gelled, also on the solvent system used. An important feature of the invention is the control of gelling time and the rate of increase in gel strength by varying the solvent system used. If the concentration of aluminium is too low, the gel obtained will not be rigid or a coherent gel will not be formed. The acetate or lactate is conveniently used in aqueous solution and the addition of a large volume of the solution of acetate or lactate must be avoided. Concentrated aqueous solutions of the acetates or lactates are therefore desirable. When a concentrated aqueous solution of an aluminiun hydroxychloride is diluted with water and mixed with a given volume of the aqueous acetate or lactate solution, the gel time increases with increasing dilution. On dilution with glycols or glycerols the gel time also increases with increasing dilution. However on dilution with monohydric alcohols, the gel time decreases with increasing dilution. This unexpected effect is of great value in the production of refractory shapes because the rate of increase of gel strength is rapid. This means that moulded articles can be removed from the mould very soon after gelation. Examples of preferred alcohols are the monohydric water-miscible alcohols methanol, ethanol and isopropanol. The preferred glycols are ethylene glycol and propylene glycol.

The most preferred aluminium hydroxychlorides are those in which $n$ is approximately 5 and $n$ is between 2 and 3. The most preferred materials have Al:Cl atomic ratio $1.9 - 2.1 : 1$. Ammonium acetate, ammonium lactate and magnesium acetate are the preferred acetates and lactates, especially for the production of shaped refractory articles.

The gel obtained may be used to bind refractory powders to produce shaped refractory articles. It may also be used in the production of shaped catalyst masses. The gel may also be used as a cement and in the binding of ceramic fibres to obtain a rigid mass. The gel is also suitable for the cementing together of vacuum formed shapes prepared from ceramic fibres. Another use for the gel is in cosmetic preparations, for instance in the preparation of anti-perspirants.

Moulds for casting metals or alloys may be prepared by dispersing a suitably graded refractory powder into an aqueous alcoholic solution of an aluminium hydroxyhalide of the above general formula in which $n$ has a value of 4 or greater and an acetate or lactate which gives an aqueous solution which is alkaline and while the dispersion is gelling, moulding the dispersion to shape during gelation, igniting the alcohol present in the gelled shape, then firing to obtain a mould, part mould or core suitable for use in the casting of metals or alloys.

The preferred aluminium hydroxychloride is available as a solid or as a 50% w/w aqueous solution. It is preferred to prepare aqueous solutions from the solid material as these solutions give gel times faster than the gel times obtained from solutions of the same aluminium concentration made by diluting the 50% w/w aqueous solution. Glycerol and ethylene glycol lengthen the gel time, whereas methanol, ethanol and isopropanol shorten the gel time.

Some gel-forming systems will initially be described by way of example:

No. 1

This uses the commercially available aluminium chlorohydrate solution which has the following properties.

| | |
|---|---|
| AlCl atomic ratio | $1.9 - 2.1 : 1$ |
| Specific gravity | $1.325 - 1.345$ |
| Alumina content | $23 - 24\%$ as $Al_2O_3$ |

A solution of ammonium acetate is used as the gel accelerating agent. A suitable solution of ammonium acetate is the strong ammonium acetate solution of the 1953 edition of the British Pharmocopoea. This solution contains $55.0 - 60.0\%$ ammonium acetate.

When 15 ml of the strong ammonium acetate solution was added to 100 ml of the aluminium chlorohydrate solution and stirred well, a rigid coherent gel was obtained in approximately four minutes.

No. 2

This is prepared by dissolving 250 grams of solid aluminium chlorohydrate in 350 ml of water and allowing the solution to stand for 24 hours before use. The aluminium chlorohydrate used is one in which $n$ is approximately 5 and $m$ is approximately 2.

When 10 ml of the strong ammonium acetate solution was added to 100 ml of the above aluminium chlorohydrate solution and stirred well, a rigid coherent gel was obtained in approximately two minutes. This gel gained strength more rapidly than did the gel obtained from No. 1 above.

No. 3

This is prepared by diluting one volume of the above No. 2 solution of aluminium chlorohydrate with one volume of ethyl alcohol, 64 O.P. I.M.S. When 10 ml of the strong ammonium acetate solution was added to 100 ml of the above aluminium chlorohydrate solution and stirred well, a rigid coherent gel was obtained in approximately 28 seconds. This gel gained strength rapidly.

An alternative gel accelerating solution is syrupy ammonium lactate solution. This contains about 60% by weight $CH_3CH(OH)COONH_4$ at 20°C. 50 ml of the alumina binder + 10 ml syrupy ammonium lactate solution gelled in 10 minutes while 50 ml of the alumina binder + 5 ml syrupy ammonium lactate solution gelled in 18 minutes.

An alternative gel-accelerating solution of magnesium acetate was prepared by dissolving 30.0 grams of $(CH_3COO)_2Mg.4H_2O$ in 100 ml water. The following gel times were observed:

50 ml alumina binder of No. 3 + 9.0 ml magnesium acetate solution — gel in 21 minutes.

50 ml alumina binder No. 3 + 15 ml magnesium acetate solution — gel in 6 minutes.

NO. 4

A binder was prepared by dissolving 75.0 grams of solid aluminium bromohydrate in 105 ml water, then adding 100 ml of ethyl alcohol, 64 O.P. I.M.S. It had the following gelation characteristics:

25 ml binder solution + 2.0 ml strong ammonium acetate solution (B.P. 1953 edition) — gel in 5¼ minutes.

25 ml binder solution + 2.5 ml strong ammonium acetate solution (B.P. 1953 edition) — gel in 2¼ minutes.

Both gels were satisfactory and developed strength well.

The said aluminium bromohydrate used was made in United States of America by Reheis. The formula is $Al_2(OH)_5Br.2-3H_2O$. The product has Al:Br atomic ratio 2.1 : 1 to 1.9 : 1.

These four gel-forming systems may be used as follows in the preparation of shaped refractory masses.

EXAMPLE A

Shaped refractory articles were prepared from tabular alumina as follows. The tabular alumina used was T-60 grade of Alcoa of Great Britain Ltd. Parts are parts by weight and the screen sizes refer to Tyler standard screen scale sieves.

| | |
|---|---|
| −8 +14 grade | 2 parts |
| −14 +28 grade | 1 part |
| −28 +48 grade | 1 part |
| −48 grade | 1 part |
| −100 grade | 1 part |

For each pound weight of the above tabular alumina mix the proportion of binder and gelation accelerator solution was as follows.

a. 45 ml of No. 1 binder solution with 7 ml of strong ammonium acetate solution.

b. 45 ml of No. 2 binder solution with 4 ml of strong ammonium acetate solution.

c. 45 ml of No. 3 binder solution with 3 ml of strong ammonium acetate solution.

The refractory powder was dispersed into the mixture of the binder solution and the ammonium acetate solution and while the dispersion was gelling, it was moulded to shape and allowed to gel. After gelation, it was allowed to dry, then fired to obtain a shaped refractory article.

For the production and properties of tabular alumina, see B. L. Bryson Jnr. Refractories Journal, November 1971, pp 6–9.

EXAMPLE B

Shaped refractory articles were prepared from the following mixtures of refractory powders. Parts are parts by weight and the screen sizes refer to British Standard sieves.

| | |
|---|---|
| −¼ +8 Molochite (Trade Mark on alumino silicate refractory aggregate, produced from a china clay subjected to a calcination at above 1500°C | 1 part |
| −8 +16 Molochite | 1 part |
| −16 +30 Molochite | 1 part |
| 100 CML P.B. Sillimanite | ⅔ part |
| −100 Fused Alumina | ⅔ part |
| Portasil G (an aluminosilicate material containing 85% $Al_2O_3$ 90% Al passes 120 mesh ASTM sieve) | ⅔ part |

For each pound weight of the above mixture of refractory powders the proportion of binder and gelation accelerator solution was as follows:

a. 50 ml of No. 1 binder solution with 7 ml of strong ammonium acetate solution.

b. 50 ml of No. 2 binder solution with 4 ml of strong ammonium acetate solution.

c. 50 ml of No. 3 binder solution with 3 ml of strong ammonium acetate solution.

The refractory powder was dispersed into the mixture of the binder solution and the ammonium acetate solution and while the dispersion was gelling, it was moulded to shape and allowed to gel. After gelation, it was allowed to dry, then fired to obtain a shaped refractory article.

EXAMPLE C

Shaped refractory articles were prepared from silicon carbide powder as follows. A mixture of silicon carbide powder was prepared by mixing Silicon carbide powder −8 +14 mesh — 1 part
Silicon carbide powder −14 +36 mesh — 1 part
Silicon carbide powder −36 +100 mesh — 1 part To two parts of the above mixture, one part of silicon carbide fines is added. The parts are parts by weight and the screen sizes refer to British Standard screens. For each pound weight of the above mixture of silicon carbide powders the proportion of binder and gelation accelerator solution was as follows.

45 ml of No. 2 binder requires 4 ml of strong ammonium acetate solution.

The refractory powder was dispersed into the mixture of the binder solution and the ammonium acetate solution and while the dispersion was gelling, it was moulded to shape and allowed to gel. After gelation, it was allowed to dry, then fired to obtain a shaped refractory article.

If desired, No. 1 binder may be used, in the proportion of 45 ml of binder solution and 7 ml of strong ammonium acetate solution per pound weight of powder mixture. No. 3 binder can also be used, in the proportion of 45 ml of binder solution and 3 ml of strong ammonium acetate solution per pound weight of powder mixture.

EXAMPLE D

Shaped refractory articles were prepared from powdered fused alumina as follows. Parts are parts by weight and the screen sizes refer to British Standard sieves.

| −3/16 | +⅛ | 7 parts |
|---|---|---|
| −8 | +16 | 23 parts |
| −16 | +22 | 30 parts |
| −100 | | 40 parts |

For each pound weight of the above mix, 40 ml of No. 2 binder solution was used, in conjunction with between 2 and 3 ml of strong ammonium acetate solution. The refractory powder was dispersed into the mixture of the binder solution and the ammonium acetate solution and while the dispersion was gelling, it was moulded to shape and allowed to gel. After gelation, it was allowed to dry, then fired to obtain a shaped refractory article.

In all of examples A-D the shaped moulding could be removed from the mould 10-15 minutes after preparation of the dispersion.

In the preparation of binder No. 3, the volume of ethyl alcohol could be replaced by one volume of methyl alcohol or one volume of isopropyl alcohol with very little effect on the gel time.

EXAMPLE E

A mixture of T60 grade tabular alumina was prepared by mixing

| −48 grade | 1 part by weight |
|---|---|
| −100 grade | 1 part by weight. |

The screen sizes refer to Tyler standard screen scale sieves.

The above tabular alumina mixture was dispersed into a mixture of No. 1 binder solution and ammonium acetate solution, the proportion being one pound weight of tabular alumina mixture to 45-50 ml of No. 1 binder solution and 7 ml of strong ammonium acetate solution. The dispersion was allowed to gel. Twenty four hours after gelation, the gelled dispersion was powdered and passed through a 48 mesh sieve. The resulting dry powder was pressed in a box 8 inch × 7 × 3½inch deep using a Butler Manufacturing & Engineering Co. Ltd. impact hammer press operating at an impact pressure of 80 p.s.i. The compact obtained was quite strong enough to handle and after firing gave a strong refractory article.

The above mixture of T60 grade tabular alumina should be used when reproduction of detail is desired. For the production of alumina bricks by the procedure described in this example, the mixture of tabular alumina given in Example A can be used.

EXAMPLE F

In the binding of ceramic fibres to obtain a rigid mass, binder solution No. 1 is convenient to use, in the proportion of 100 ml of the chlorohydrate solution to 12-15 ml of the strong ammonium acetate solution. "Triton Kaowool" ceramic fibre blanket, thickness one inch, is impregnated with a mixture of binder solution No. 1 and strong ammonium acetate solution in the proportion given above, then compressed to a thickness of ¾, the binder being allowed to gel during the compression operation. A rigid thermal insulating material was obtained.

EXAMPLE G

When using binder No. 3 a preferred procedure for the production of refractory articles of intricate shape is to increase the amount of liquid used per pound weight of refractory powder. With the mixture of refractory powders given in Example B, suitable proportions are 60-70 ml of binder No. 3 and 3.6 - 4.2 ml of strong ammonium acetate solution. For the mixture of tabular alumina powders given in Example A, 60 ml of Binder No. 3 and 3.6 of strong ammonium acetate solution should be used per pound weight of alumina powder. While the object is gaining strength, exposed surfaces may be protected by coating with a solution of paraffin wax in carbon tetrachloride. This prevents cracking due to alcohol evaporation.

EXAMPLE H

The procedure of Example G may be used to prepare moulds, part moulds or cores suitable for use in the casing of metals or alloys.

Using the mixture of refractory powders given in Example B, with a proportion per pound of powder of 70 ml of binders No. 3 and 4.2 ml of strong ammonium acetate solution, a slurry was prepared and poured over a pattern contained in a suitable mould box. When the slurry had gelled, the gelled shape was removed from the pattern and mould box.

The alcohol present was then ignited, so that the alcohol burned evenly from all exposed surfaces. When the alcohol had finished burning, the shape was fired, giving an object, (mould, part mould or core), suitable for use in the casting of metals or alloys.

EXAMPLE I

Crucibles made from 1lb tabular alumina mix, with 6 ml of the alumina binder of No. 3 + 6 ml syrupy ammonium lactate solution. This is very fluid, necessary for thin-walled crucibles. The gel-time of the slurry is about 25 minutes. It is desirable to leave for a minimum of 30 minutes after gelation before moving core and stripping from mould.

The tabular alumina mix used was T60 tabular alumina (parts by weight)

| 8-14 (Tyler Standard Screen sizes) | 1 part |
|---|---|
| 14-28 (Tyler Standard Screen sizes) | 1 part |
| 28-48 (Tyler Standard Screen sizes) | 1 part |
| 48F (Tyler Standard Screen sizes) | 1½ parts |

EXAMPLE J

Zircon/Zirconia crucibles were prepared as follows:

A mix of zircon and zirconia was made from

| Zircon sand | 7 parts by weight | (all passing 60 mesh B.S. 410) |
|---|---|---|
| Zircon Flour | 2 parts by weight | (all passing 200 mesh B.S. 410) |
| Zirconia | 1 part by weight | (all passing 200 mesh B.S. 410) |

To 1lb 13oz. of the above mix 1lb of zircon grog was added. (The zircon grog was size ¼ to dust, obtained by crushing old zircon bricks). 100 ml of the alumina binder of No. 3 and 30 ml of the magnesium acetate solution were used. The crucibles were allowed to air-dry for three days, then fired at 1550°C for 8 hours. They were all sound, with a good "ring", suggesting that 1550°C is a practicable minimum firing temperature.

This example provides a source of magnesia for stabilisation of a zirconia bonded with the alumina gel.

Zircon/Zirconia crucibles may also be prepared by using with the above refractory powder 120 ml of alumina binder No. 3 and 12 ml of an accelerator solution prepared by diluting 60 ml of strong ammonium acetate solution (B.P. 1953 edition) with 40 ml of water. The crucibles were allowed to air-dry for 3 days then fired at 1550°C for 8 hours.

EXAMPLE K

Shaped refractory articles are provided from the following refractory powders.

| Molochite | ¼ - 8 | 2 parts |
|---|---|---|
| | 8 - 16 | 3 parts |
| | 16 - 30 | 4 parts |
| | - 120 | 3 parts |
| Zircon sand | | 4 parts all passing 60 mesh B.S. 40 |

The parts are by weight. Use 1lb 10 ozs. of the above mix with 100 ml alumina binder No. 3 and 10 ml accelerator (diluted). This gives an extremely good crucible on firing to 1550°C. Firing at 1500°C might be acceptable.

EXAMPLE L

Tabular alumina powder (Example I) was dispersed into a mixture of alumina binder solution No. 4 and strong ammonium acetate solution, to give a slurry which was poured into the mould. The proportions used were 1lb of tabular alumina mix with 45 ml of the binder solution and 4 or 5 ml of strong ammonium acetate solution. The resulting crucible could be removed from the mould in 10 minutes after pouring. After air-drying, the crucibles were fired to 1650° for eight hours.

EXAMPLE M

Fused alumina powder (Example D) was dispersed into a mixture of the alumina binder solution No. 4 and strong ammonium acetate solution, to give a slurry which was poured into the mould. The proportions used were 1lb of the fused alumina powder mix with 45 ml of the binder solution and 5 ml of strong ammonium acetate solution. The resulting crucible could be removed from the mould in 10 minutes after pouring. After air-drying, the crucibles were fired to 1650°C for 8 hours.

EXAMPLE N

Fused alumina powder (Example D) was dispersed into a mixture of No. 3 binder solution and strong ammonium acetate solution, to give a slurry which was poured into the mould. The proportions used were 1lb of the fused alumina powder mix with 45 ml of the No. 3 binder solution and 1.8 – 2.0 ml of the strong ammonium acetate solution. The resulting crucibles could be removed from the mould in 15 – 20 minutes after pouring. After air-drying, the crucibles were fired to 1650°C for 8 hours.

EXAMPLE O

A mix of fused mullite grains for manufacturing crucibles was prepared as follows:

| 3/6 – ¼ | 7 parts |
|---|---|
| ¼ – 1/16 | 23 parts |
| 1/16 – 22 mesh | 30 parts |
| – 100 mesh | 40 parts |

The parts are by weight and the mesh sizes are B.S. 410 sieves.

To make the crucibles, 12 oz of the above mix were used with 45 ml of No. 3 and 2 ml of strong ammonium acetate solution. The resulting crucible could be removed from the mould 15 – 20 minutes after pouring. After air-drying, the crucibles were fired to 1500°C.

A sintered mullite may be used instead of the fused mullite. The properties of the fused and sintered mullite used are described by Sargeant, Isherwood and Atthis, Refractories Jnl., 1973, June, pp 12 – 18.

EXAMPLE P

"Triton Kaowool" ceramic fibre blanket is formed into rigid shapes by impregnating the blanket with binder No. 3. Excess solution is removed by squeezing the impregnated blanket, which is now shaped as required. The binder is set by heating at 80°–110°C. Heating is continued until the shape is dry and rigid. The temperature should be gradually raised to 110°C during the heating time. "Triton Kaowool" ceramic fibre blanket can be formed into rigid shapes by impregnating the blanket with Alumina binder No. 3 to which has been added a small amount of strong ammonium acetate solution (B.P. 1953 edition). Excess solution is removed by squeezing the impregnated blanket, the binder being allowed to gel during the compression operation. Not more than 5 ml of strong ammonium acetate solution per 100 ml of binder No. 3 should be used.

EXAMPLE Q

The preferred binding agent is No. 3 binder and the gelation accelerator is prepared by diluting 60 ml of strong ammonium acetate solution (British Pharmacopea 1953) with 40 ml of water. For 1lb of the previously given preferred refractory powder composition 60 ml of the No. 3 binder are used and 8 ml of the accelerator solution. The gel time of the slurry is about 15 minutes. It is desirable to leave the article in the mould for at least 15 to 30 minutes after gelation before any cores are removed and the mould stripped. The articles are air-dried overnight and then fired to at least 1550°C, preferably to 1620°C.

EXAMPLE R 20 ml of binder No. 2 and 30 ml of ethyl alcohol 64 O.P. industrial methylated spirit were mixed and to this mixture was added 5.0 ml of strong ammonium acetate solution (British Pharmacopoea 1953 edition). The gel time observed was 16 seconds, the gel gaining strength rapidly. A similar result was obtained when the volume of ethyl alcohol added was replaced by the same solution of methyl alcohol or isopropyl alcohol. When the volume of ethyl alcohol added was replaced by the same volume of ethylene glycol or glycerol, the gel time was lengthened and the gel gained strength only slowly.

We claim:

1. A method of producing a shaped refractory article comprising.

a. forming a castable gelable slurry by combining (1) a refractory aggregate; (2) a binder solution comprised of an aluminum hydroxyhalide of the formula $Al_2(OH)_N X_{(6-N)} \cdot mH_2O$ or a polymer thereof wherein n is a number less than 6, m is a number less than 4 and X is a chlorine, bromine or iodine atom, said aluminum hydroxyhalide being dissolved in water or a mixture of water and an alcohol, glycol, polyglycol or glycerol; and (3) an aqueous solution of ammonium acetate, ammonium lactate or magnesium acetate;

b. allowing said slurry to gel to a self-supporting state while maintaining it in the desired shape; and c. then drying and firing the resulting article.

2. A method of claim 1 wherein the aluminum hydroxyhalide includes a substantial proportion of an aluminum hydroxychloride wherein n has a value of 4 or greater.

3. A method of claim 2 wherein the aluminum hydroxyhalide has an aluminum : halide ratio of 1.9–2.1 : 1.

4. A method of claim 1 wherein n is 5 and m is 2 or 3.

5. A method of claim 1 wherein the aluminum hydroxyhalide includes a substantial proportion of an aluminum hydroxychloride wherein n has a value of 4 or greater.

6. A method of claim 5 wherein the aluminum hydroxyhalide has an aluminum : halide ratio of 1.9;14 2.1 : 1.9–

7. A method of claim 1 wherein $n$ is 5 and $m$ is 2 or 3.

8. A method of claim 7 wherein the aluminum hydroxyhalide has an aluminum : halide ratio of 1.9–2.1 : 1.

9. A method of claim 1 wherein said acetate or lactate is ammonium acetate.

10. A method of claim 1 wherein said acetate or lactate is ammonium lactate.

11. A method of claim 1 wherein said aluminum hydroxyhalide is dissolved in a mixture of water and methanol, ethanol or isopropanol.

12. A method of claim 11 wherein said drying is effected by burning off alcohol contained in said article.

* * * * *

UNITED STATES PATENT AND TRADEMARK OFFICE
CERTIFICATE OF CORRECTION

PATENT NO. : 3,975,202
DATED : August 17, 1976
INVENTOR(S) : Harold Garton Emblem et al.

It is certified that error appears in the above-identified patent and that said Letters Patent are hereby corrected as shown below:

Claim 1, column 9, line 5, delete ".".

Claim 1, column 9, line 9, delete "$Al_2(OH)_N X_{(6-N)} \cdot mH_2O$" and insert therefor --$Al_2(OH)_n X_{(6-n)} \cdot mH_2O$--.

Claim 6, column 10, lines 8-9, delete "1.9;14 2.1 : 1.9-" and insert therefor --1.9-2.1 : 1.--

Signed and Sealed this

Twenty-eighth Day of December 1976

[SEAL]

*Attest:*

RUTH C. MASON
*Attesting Officer*

C. MARSHALL DANN
*Commissioner of Patents and Trademarks*